United States Patent [19]
Page et al.

[11] Patent Number: 5,523,222
[45] Date of Patent: Jun. 4, 1996

[54] POLYELECTROLYTE DNA CONJUGATION AND GENETIC TRANSFORMATION OF AN ANIMAL

[75] Inventors: Raymond L. Page, Christiansburg; William H. Velander; John L. Johnson, both of Blacksburg, all of Va.

[73] Assignee: Virginia Tech Intellectual Properties, Inc., Blacksburg, Va.

[21] Appl. No.: 286,495

[22] Filed: Aug. 5, 1994

Related U.S. Application Data

[63] Continuation of Ser. No. 17,724, Feb. 16, 1993, abandoned.

[51] Int. Cl.$^6$ .............................. C12N 5/00; C12N 15/00
[52] U.S. Cl. .................................. 435/172.3; 435/172.1; 800/2; 800/DIG. 1; 935/52; 935/53
[58] Field of Search ............................. 435/172.1, 172.3, 435/240.2; 800/2, DIG. 1; 514/44; 935/52, 53

[56] References Cited

U.S. PATENT DOCUMENTS

| | | | |
|---|---|---|---|
| 4,873,191 | 10/1989 | Wagner et al. | 435/172.3 |
| 5,166,320 | 11/1992 | Wu et al. | 530/395 |

OTHER PUBLICATIONS

Brinster et al., "Somatic Expression of Herpes Thymidine Kinase in Mice following Injection of a Fusion Gene into Eggs", *Cell*, vol. 27 223–231 (Nov. 1981) Pt. 2.
Campbell et al., "Comparison of the Whey Acidic Protein Genes of the Rat and Mouse", *Nucleic Acids Research*, vol. 12, No. 22 (1984).
G. Y. Wu et al., *Journal of Biological Chemistry*. vol. 263, No. 29, issued 15 Oct. 1988, "Receptor–Mediated Gene Delivery and Expression in Vivo" pp. 14621–14624.
W. G. Chaney et al., *Somatic Cell and Molecular Genetics*, vol. 12, No. 3, issued 1986, "High Frequency Transfection of CHO Cells Using Polybrene", pp. 237–244.
A. V. Kabanov et al., *Biopolymers*, vol. 31, isused 1991, "DNA Interpolyelectrolyte Complexes as a Tool for Efficient Cell Transformation", pp. 1437–1443.
B G Brackett et al (1971) Proc Natl Acad Sci USA 68: 353–357.
M R Capecchi (1980) Cell 22:479–488.
F E Farber et al (1975) Biochim Biophys Acta 390:298–311.
N M Antonelli et al (1990) Theor Appl Genet 80:395–401.

*Primary Examiner*—Jacqueline M. Stone
*Assistant Examiner*—Bruce R. Campbell
*Attorney, Agent, or Firm*—Seidel Gonda Lavorgna & Monaco

[57] ABSTRACT

The present invention provides a method of obtaining an organism which has been characterized as having cells containing exogenous genetic material which includes any sequence of DNA that can be distinguished as exogenous by known molecular biological analysis by insertion of genetic material into an animal's genetic makeup. The insertion of the genetic material is done by inserting DNA that has been complexed with molecules that allow the DNA to be inserted into the chromosomes when injected into the cytoplasm, perivitelline space, or placed in surrounding culture media to be taken up and incorporated into the genome. When the DNA is complexed into the polyelectrolyte molecules by electrostatic attraction, the electric charge of DNA of the complex is partially to substantially neutralized. The present method does not require the genetic material to be introduced into the embryo at a particular stage in development.

14 Claims, 6 Drawing Sheets

POLYELECTROLYTE DNA CONJUGATION AND GENETIC TRANSFORMATION OF AN ANIMAL

This is a continuation of application Ser. No. 08/017,724 filed on Feb. 16, 1993 abandoned.

FIELD OF THE INVENTION

The invention relates to a method of inserting genetic material into an animal's genetic makeup with a DNA/polyelectrolyte complex. The invention relates to the field of genetics, in general, and more specifically to a method for altering genetic material of an organism.

BACKGROUND OF THE INVENTION

The transfer of genetic material (DNA) from one species to another has been a focus of research for years. Transgenic animals are animals containing transferred exogenous genetic material which is passed on to their offspring. Once founder animals are established, they pass transgenic traits on to some, or all, of their offspring.

Manufacture of improved foods and agricultural products has been a focus of transgenic technology. One aim of transgenic technology is the production of useful recombinant proteins in milk or blood of farm animals.

Transgenic technology has also enabled in vivo study of gene expression. The in vivo results may often be directly related to a specific disease process, thus yielding a greater understanding of the disease process. Transgenic animals may also be used for the production of transplant organs which do not cause the usual immunogenic reactions in a recipient, e.g., a human recipient.

The potential for transferring genetic material into mammalian cells cultured in vitro has existed for many years. However, gene transfers into whole mammalian organisms have only recently been practicable.

Mosaic mice (i.e., non-transgenic mice having exogenous DNA in some of their tissue) have been produced by injection of tetracarcinoma cells into the blastocysts of developing mice (Brinster, R. L., *J. Exp. Med.*, 140: 1049–1056 (1974); Mintz et al., *Proc. Natl. Acad. Sci. U.S.A.*, 72: 3585–3589 (1975); and Papaioannou et al., *Nature*, 258: 69–73 (1975)). Teratocarcinoma cells have also been used as vehicles for introducing genes into mice to produce mosaic mice. (See, for example, Pellicer et al., *Proc. Natl. Acad. Sci. U.S.A.*, 77: 2098–2102 (1980)).

Mosaic mice produced by the above methods have reduced germline transmission. This is due to the mosaic mice that develop as males being unable to produce sperm.

Liposome technology (anionic and cationic) has provided efficient genetic transformation of mammalian cells cultured in vitro. As a logical extension of in vitro technology, several researchers have attempted to generate transgenic animals via liposomes complexed with DNA. These attempts employed both conventional mammalian cell transfection techniques and microinjection into the cytoplasm and perivitelline space. No transgenic animals resulted. See, e.g., Loskutoff, et al., *Theriogenology*, 25, 169 (1986); or Reed, et al., *Theriogenology*, 25, 293 (1988).

Another advance in non-embryonic in vitro mammalian cell transfection technology uses normal cellular processes, such as receptor-mediated endocytosis, to incorporate DNA into mammalian cells. Endocytosis has enabled insertion of genetic material into an in vitro non-embryonic cellular genome. Wu et al., *J. Biol. Chem.*, 263, 14621–14624 (1988) covalently linked a ligand for a specific cell-surface receptor to polylysine (a polycation which binds DNA by electrostatic interaction). The polylysine ligand-complex was allowed to bind DNA. Cells were then incubated with the polylysine-ligand/DNA complex, which resulted in the uptake and expression of the exogenous DNA. However, the exogenous DNA was not incorporated into the host cell's genome. The polylysine served as a bridge between the DNA and the ligand for a specific cell surface receptor. The cell surface receptor was a critical component, since it was required for endocytic absorption of the DNA.

The invention of embryonic stem cell technology has made it possible for the first time to transfer DNA into an intact mammal. Genetic transfers with stem cells have been severely limited because obtaining stem cells and making gene transfers is labor-intensive and costly. Stem cells must be cultured in vitro for long periods of time. The result is usually germline mosaic animals. Stem cell technology has the further limitation of only having been successfully demonstrated in mice. Consequently, this technology cannot yet be applied to the generation of farm animals where gene transfers would have important practical applications.

DNA has been inserted, by microinjection, directly into a non-germ cell being cultured in vitro, (Capecchi, M. *Cell*, 22: 479–488 (1980)). The technique was later extended to pronuclear microinjection of an early embryo to produce transgenic animals. (Wagner, et al. *Proc. Natl. Acad. Sci. U.S.A.* 78, 6376–6380 (1981)).

Pronuclear microinjection of DNA produces fertile transgenic animals, which may yield offspring having the transgenic trait. However, there are significant disadvantages with pronuclear microinjection.

An important negative side effect of pronuclear microinjection is a dramatic reduction in the embryonic viability of microinjected embryos. Pronuclear micro-injected embryos show a significant loss in embryonic viability as compared to uninjected embryos.

Brinster, et al., *Proc. Natl. Acad. Sci. U.S.A.* 82, 4438–4442 (1985) compared cytoplasmic injection of plain buffered DNA to pronuclear injection of the same material. While cytoplasmic injection was found less detrimental to in vitro embryo survival than pronuclear injection, it was not recommended for producing transgenic mice. Cells from only 2 embryos of the 224 fetuses examined tested positive for the foreign DNA. Only fetal cells were tested for the foreign DNA, and no transgenic live pups were produced by cytoplasmic injection. Importantly, the embryos were not tested for mosaic traits versus true transgenic traits.

In further cytoplasmic microinjection attempts, neither the Brinster, et al. authors or other researchers (e.g., King, et al., *Mol. Reprod. Dev.* 1, 57–62 (1988)) have been able to duplicate the above results. No exogenous DNA has been detected in animal cells or tissues, which have arisen from embryos injected with just the exogenous naked DNA in a buffer. This raises the possability that the result reported by Brinster, et al., *Proc. Natl. Acad. Sci. U.S.A.* 82, 4438–4442 (1985) is a false positive for transgenic DNA.

Accordingly, there is a need for a method which provides greater viability of embryos. Greater viability would be particularly important in producing transgenic farm animals such as sheep, goats and cows. Transgenic animals from these species are difficult to efficiently produce, since they only have a small number of offspring at a time (from 1 to 4). Further, there is a need for an improved method for producing transgenic species where pronuclei are difficult to see (e.g., sheep, goats, cows, fish, or birds). For those species, a method of gene transfer not requiring a visualized pronucleus would be desired.

SUMMARY OF THE INVENTION

The present invention provides a method for inserting a DNA segment into the genome of a recipient organism comprising:

forming an electrostatic complex of polycation and DNA, wherein the polycation is present in the complex in an amount effective to neutralize the negative electric charges of the DNA of the complex to a degree sufficient to allow insertion of DNA into a chromosome of the recipient organism, inserting the polycation/DNA complex into the recipient organism's genome by injecting the complex into the cytoplasm or perivitelline space of a cell of the organism.

Preferably, genetic transformation of the organism is achieved by inserting the polycation/DNA complex by microinjection into the cytoplasm of an embryonic cell. More preferred is where the polycation/DNA complex is inserted into a one-celled animal zygote; or into a haploid animal cell selected from the group consisting of an animal sperm, an animal spermatocyte, an animal polar body, an animal oocyte, or an animal unfertilized egg. Even more preferred is where the polycation/DNA complex is inserted directly into the cytoplasm of a one-celled animal zygote, or an animal unfertilized egg. If the recipient cell is a haploid animal cell, after injection it is preferred to expose the haploid recipient cell to another haploid animal cell under conditions such that a one-celled animal zygote is formed. Most preferred is wherein the recipient cell is a one-celled animal embryo.

A polycation/DNA complex preferred for insertion has a polycation/DNA molar charge ratio of from about 5:1 to about 0.25:1, more preferably a molar charge ratio of from about 2:1 to about 0.5:1. Most preferred is a molar charge ratio about 1:1. The preferred polycation is polylysine, particularly poly(L-lysine).

In a second embodiment, the present invention provides a method for inserting a DNA segment into the genome of a recipient organism comprising:

forming an electrostatic complex of a polycation and a DNA segment, wherein the polycation is present in the complex in an amount effective to modify the DNA segment electric charge to a degree sufficient to allow insertion of the DNA segment into a chromosome of the recipient organism, inserting the polycation/DNA complex into the recipient organism's genome by placing the complex in culture medium surrounding a recipient cell, whereby the complex is taken up by at least one recipient cell and incorporated into the recipient cell genome.

A preferred recipient organism is a organism such as a mammal, fish, or bird. Examples of mammals are a laboratory rodent, a non-human primate, a rabbit, a pig, a sheep, a cow, a goat, a dog, a cat, or a horse. Preferably, the mammal is a non-human animal. Examples of a bird are a chicken, a turkey, or a duck.

(a) DNA from twenty-six mice produced by cytoplasmic injection of 15 µg/ml whey acidic protein/protein C (WAPPC-3) DNA complexed with polylysine at a 2:1 molar charge ratio (lanes 1–26);

(b) DNA from an F2 generation mouse (a progeny of a transgenic WAPPC-3 founder mouse produced by pronuclear injection) at 10,000, 1,000, 100, and 10 genome copies of transgenic mouse DNA used as a control (lanes 27–30);

(c) DNA from the same mice whose DNA corresponds to lanes 1–13 (described above) amplified by PCR with endogenous mouse WAP gene oligonucleotide primers to provide PCR controls (lanes 31–45); and (d) Control mouse DNA at a concentration of 10,000 genome copies (lanes 46–48).

Figure 1:
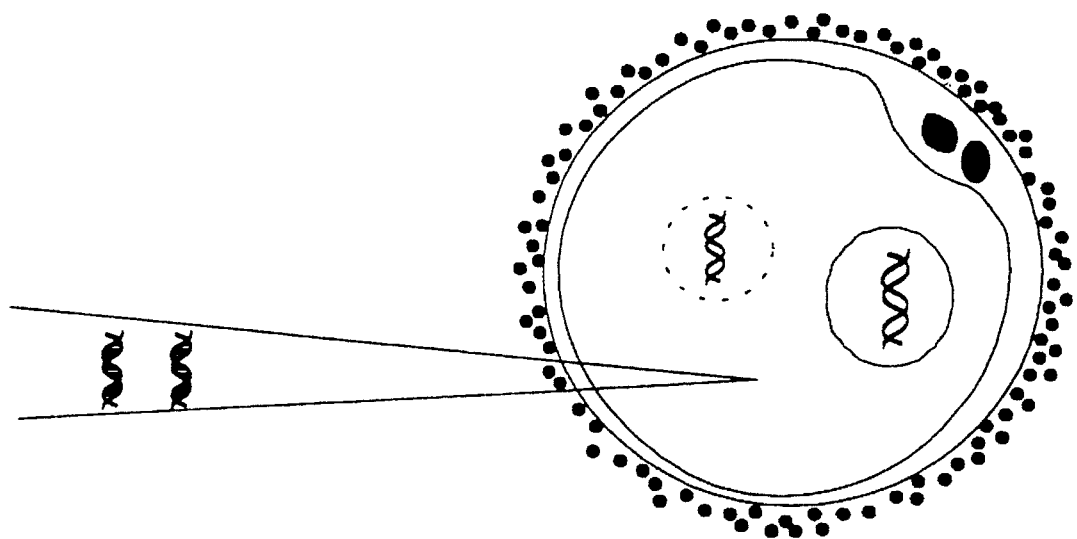
FIG. 1 is a diagram illustrating cytoplasmic injection of a polycation/DNA complex into a one-celled zygote.
Figure 2:
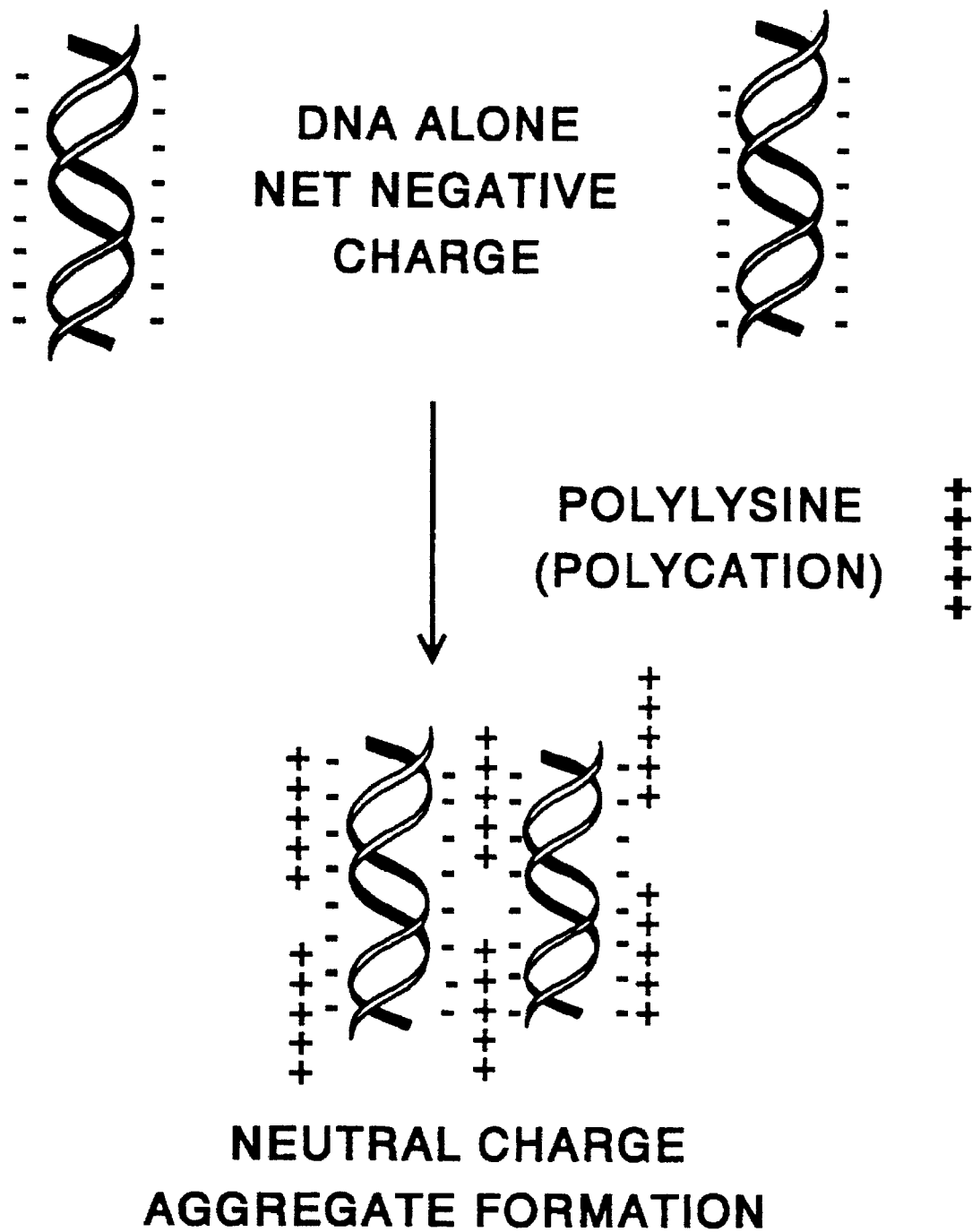
FIG. 2 is a diagram of a polycation/DNA complex being formed from polycations and DNA.
Figure 3:
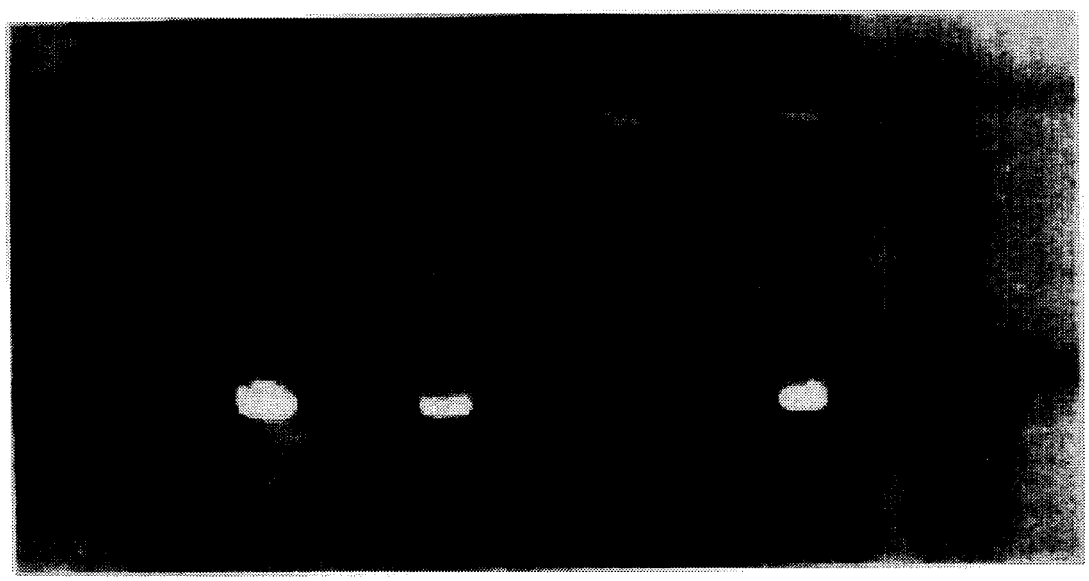
FIG. 3 is a photograph of an agarose gel showing the migration of naked DNA and the lack of migration of polycation complexed DNA. Lane 1 contains 150 nanograms of WAPPC-3 construct (DNA segment having a human protein C (hPC) coding sequence and whey acidic protein (WAP) regulatory sequences). Lane 2 and 4 contain a polycation/DNA complex formed from polylysine and 150 nanograms of WAPPC-3 construct at a molar charge ratio of 1:1. Lane 3 contains a polycation/DNA complex formed from polylysine and 150 nanograms of WAPPC-3 construct at a molar charge ration of 2:1.
Figure 4:
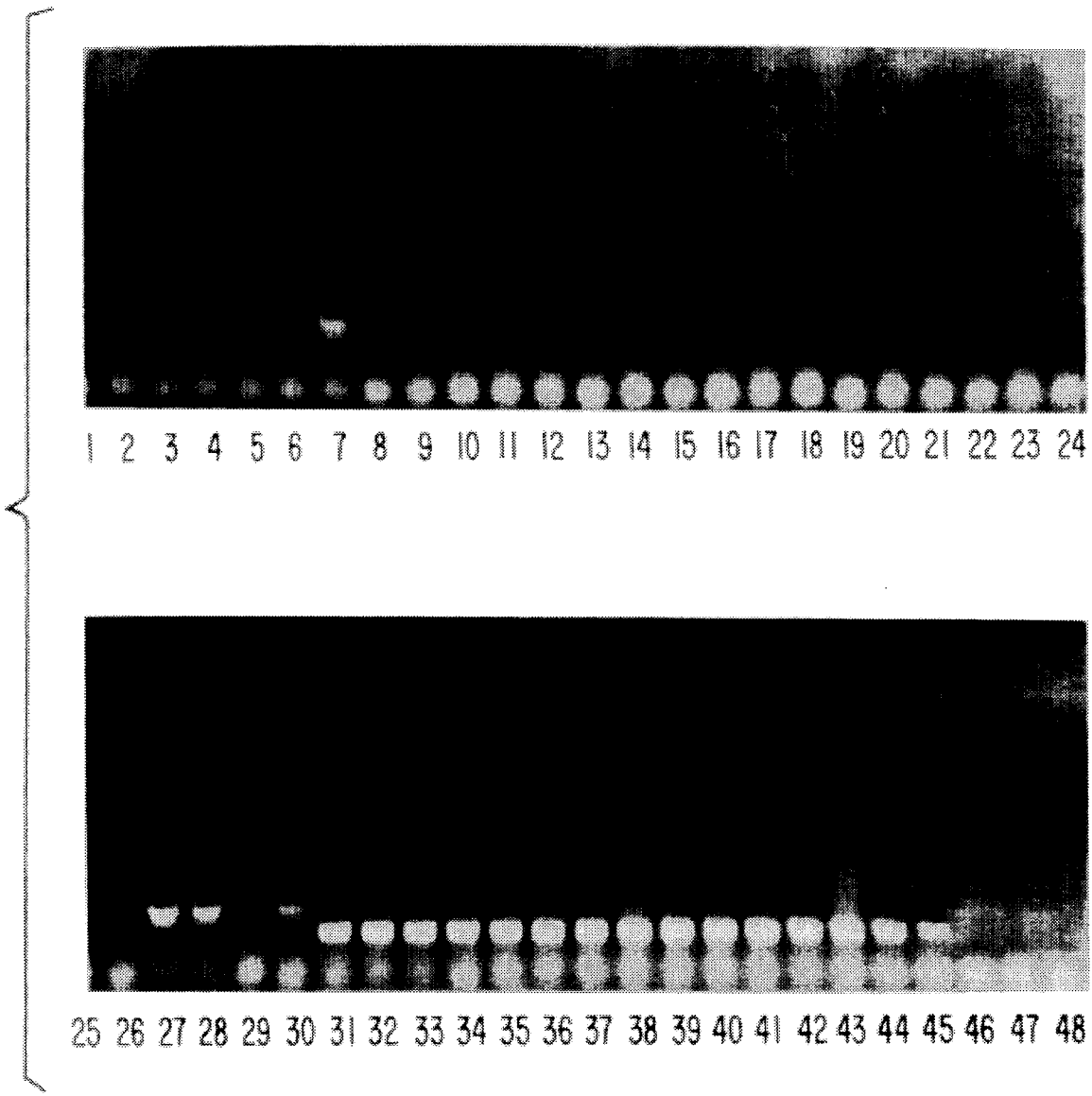
FIG. 4 is a photograph of an electrophoresis agarose gel, which shows the migration and separation of DNA amplified by polymerase chain reaction (PCR) using oligonucleotide primers specific for the WAPPC-3 construct. The template DNA, which was amplified, was extracted from mice which resulted from cytoplasmic injection of a polylysine/ WAPPC-3 complex, DNA of control non-transgenic mice, and control non-transgenic mice. The DNA in the lanes 1–48 of the photograph correspond to the following.
Figure 5:
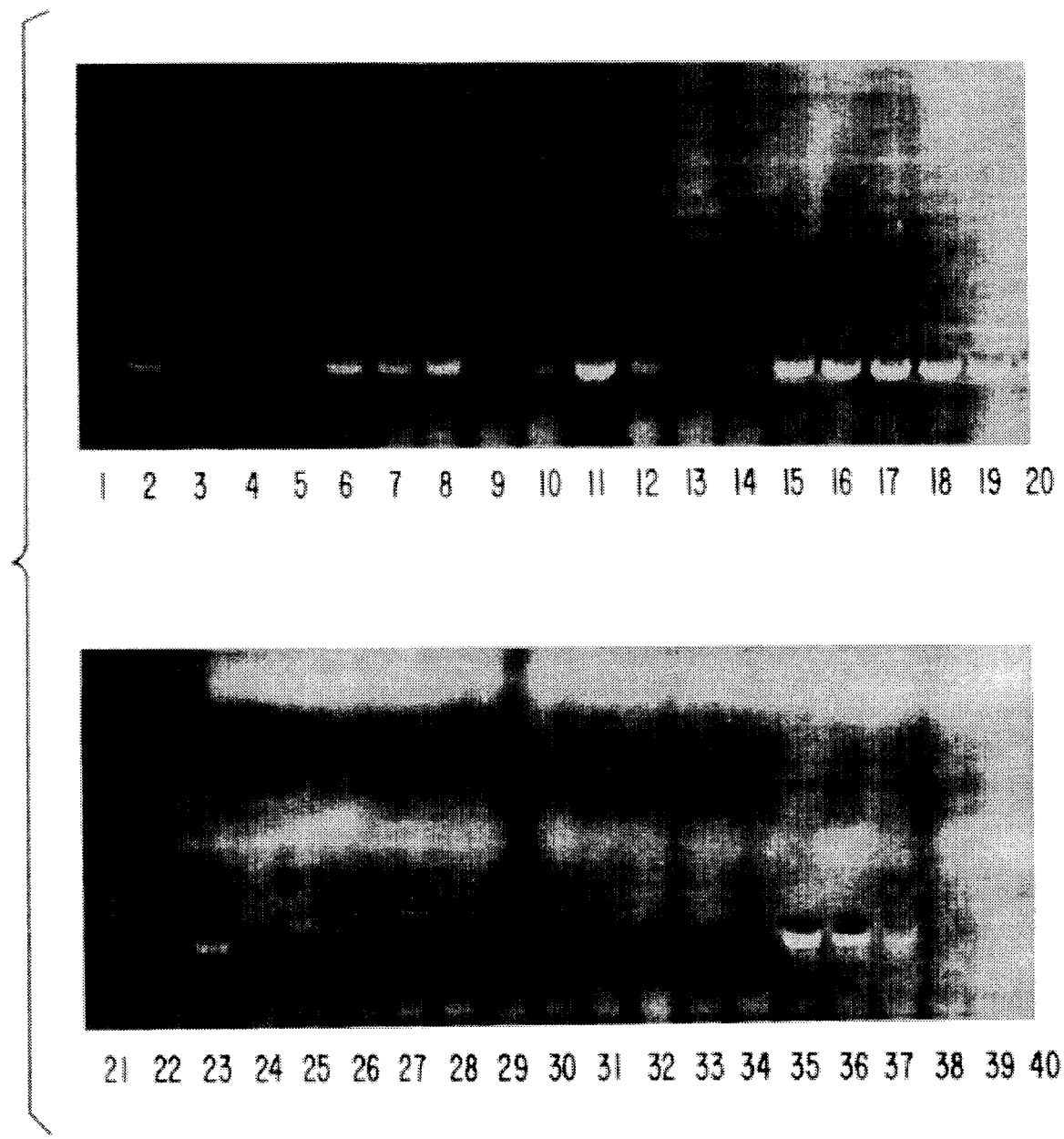

FIG. 5 is a photograph of an electrophoresis agarose gel showing DNA in the lanes of the photograph corresponding to the following:

(a) DNA from nine F1 generation mice which are progeny of a founder mouse produced by pronuclear micro-injection of 1.5 µg/ml of WAPPC-3 DNA (lanes 1–9). These are additional controls for positive PCR amplification;

(b) DNA from eleven F1 generation mice (lanes 10–20), which are progeny of founder mouse #46 obtained by cytoplasmic injection of a polycation/DNA complex at a DNA concentration of 15 µg/ml and a 1:1 molar charge ratio;

(c) DNA from fourteen F1 generation mice (lanes 21–34), which are progeny of founder mouse #7 obtained by cytoplasmic injection of a polycation/DNA complex at a DNA concentration of 15 µg/ml and a 2:1 molar charge ratio; and (d) Control DNA from an F2 generation mouse (which is the progeny of a transgenic WAPPC-3 founder mouse produced by pronuclear injection) at 10,000, 1,000, 100, and 10 genome copies of transgenic mouse DNA (lanes 35–37).

Figure 6:
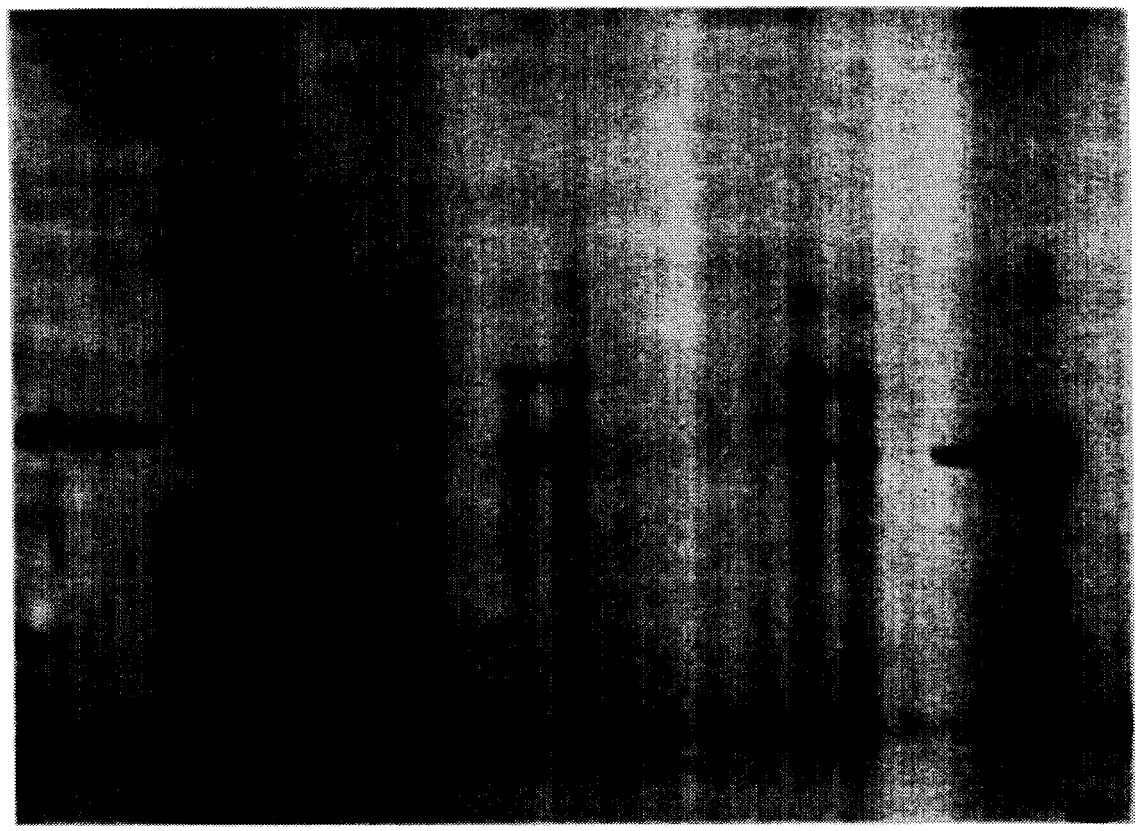

FIG. 6 is a photograph of an X-ray film from a Southern blot of DNA from mice that were made by cytoplasmic injection with polycation/WAPPC-3, DNA from a control mouse, and a transgene DNA segment for a concentration control. Lanes 1–3 and 20–22 are blots of control transgene DNA at concentrations of 250 picograms (pg), 25 pg, 5 pg, 5 pg, 25 pg, and 250 pg, respectively. Lane 4 is a blot of control mouse DNA. Lanes 5–19 are blots of cytoplasmic-injected mouse DNA from mouse numbers 119–133, respectively. Lanes 5–7, 9, 11–12, and 17–18 (corresponding to mouse numbers 119–121, 123, 125–126, and 131–132, respectively) are positive for transgenic DNA. Thus, mouse numbers 119–121, 123, 125–126, and 131–132 in the Southern blot are transgenic mice produced by cytoplasmic injection of polycation/DNA complexes.

DETAILED DESCRIPTION OF THE INVENTION

The terms listed below are defined as to their meaning when used in the above text, the following text, and in the claims.

"Recipient cell" means (1) a cell of a zygote, (2) a germ cell or polar body, or (3) a germ precursor cell, such as an oocyte or spermatocyte. The recipient cell may be a plant cell or an animal cell.

"Embryo" means either a single diploid cell (one-celled zygote) or a cleaved embryo. The embryo may have arisen from either the plant or animal kingdom. The animal embryo may have developed in vivo or in vitro to any interim stage before implantation into uterine tissue has taken place. The early pre-implantation animal embryo may have been fertilized either by natural, artificial, or in vitro insemination, or may have resulted from fusing two haploid cells.

"Exogenous genetic material" means a DNA segment that is not native to the organism being transformed by the techniques of the invention, or is an extra copy of a native DNA segment.

"Polycation" means any polymeric cationic molecule capable of forming a complex with DNA by electrostatic attraction. The polycation will typically have a net positive charge at the pH for forming a complex with DNA.

"Polycation/DNA complex" means a complex comprising a polycation and a DNA segment, formed by electrostatic attraction between the polycation and the DNA segment.

"Molar charge ratio" for a polycation/DNA complex (or for an uncomplexed mixture of polycation and DNA) means the number of moles of positive charge donated by the polycation per number of moles of negative charge arising from the DNA. For example, a 1:1 molar charge ratio results from adding enough polycation to a DNA solution such that the mixture or complex of polycation and DNA has essentially no net charge.

"Embryonic viability" means the number of embryos having an inserted DNA segment which reach the expanded blastocyst embryonic stage divided by the starting number of embryos. True embryonic viability is verified with a control ratio obtained from native embryos exposed to the same culture conditions, which accounts for losses due only to culture conditions.

"Naked DNA" means DNA alone or DNA in a carrier, i.e., DNA that has not been complexed with a polycation.

The present invention provides for the genetic transformation of either plant or animal organisms by insertion of exogenous DNA. The exogenous DNA is in the form of a polycation/DNA complex, which is inserted into the cytoplasm or perivitelline space of a recipient cell.

Exogenous DNA is inserted into an organism by injection into a zygote or haploid cell, or by placing the polycation/DNA complex in a culture of the zygote or haploid precursor cell in such a manner that the DNA is taken up and incorporated into the zygote or precursor cell. Incorporation by either injection or absorption insertion results in a transgenic zygote or transgenic haploid cell. If a cell incorporating the exogenous DNA is haploid, it is later joined with another haploid cell to form a transgenic zygote. Either type of transgenic zygote results in a transgenic organism.

The developmental timing of the addition of exogenous DNA is not critical. However, to minimize genetic mosaicism, exogenous DNA usually would not be added to multicelled embryos. It is not necessary that the transformation be carried out on a zygote. However, exogenous DNA is advantageously inserted into a single-cell zygote (fertilized egg). The polycation/DNA complex may also be inserted or absorbed into the cytoplasm of a haploid cell, which is a zygote precursor cell. A zygote precursor cell may be a germ cell (sperm, egg, or polar body) or a germ precursor cell (spermatocyte or oocyte). This also gives rise to a transgenic animal by joining a transgenic germ cell with another germ cell to produce a transgenic embryo.

The electrically charged nature of the exogenous DNA has been altered sufficiently by the polycation material of the complex to cause the DNA to be taken up by the cell and/or the genetic material of the cell. Alteration of the charge is sufficient to allow such that genetic transformation can occur, whether by injection or by absorption of the polycation/DNA complex.

For absorption, a recipient cell is exposed to a polycation/DNA complex in culture medium for sufficient time (called incubation time) to allow for absorption onto the membrane such that transport of the complex to the region of the pronucleus or nucleus can occur. The amount of time required to achieve insertion of exogenous DNA will vary depending on the cell type: embryo, egg, oocyte, polar body, sperm, or spermatocyte.

An exogenous DNA segment for cytoplasmic insertion into cells by injection or cellular absorption may be obtained by standard procedures well-known in the art. The exogenous DNA segment is referred to below as a DNA segment or a DNA construct.

A DNA segment for insertion may be purified or extracted from native DNA such as whole or partial chromosome preparations. It may be synthesized chemically, enzymatically, or biologically by in vitro techniques such as PCR, and may optionally contain native gene regulatory or structural elements.

The DNA segment for insertion may also have segments obtained from a plasmid, virus, or phage used for cloning the DNA. For example, an exogenous DNA segment comprising a gene may be obtained and cloned using standard protocols to produce a plasmid (See, e.g., Maniatis, et al., Molecular cloning: A Laboratory Manual (Cold Spring Harbor Laboratory, Cold Spring Harbor, N.Y.) (1982)).

If necessary, multiple copies of the plasmid produced for insertion or absorption are produced by polymerase chain reaction (PCR) or cloned and grown in a host. If grown in a host, the plasmid is isolated by standard lysis procedures (Maniatis, et al., Molecular Cloning: A Laboratory Manual (Cold Spring Harbor Laboratory, Cold Spring Harbor, N.Y.) (1982)) and purified. Accordingly, the host cell walls are disrupted to release the plasmids. Examples of standard lysis procedures are lysozyme/Triton X-100 lysis or lysozyme/alkaline lysis. After lysis, the plasmids having the exogenous DNA can then be isolated and purified from the lysis solution. For example, exogenous DNA may be isolated and purified by electrophoresis or banding on ethidium bromide/cesium chloride gradients.

The exogenous DNA for insertion may be isolated from a cloning vector by digesting away cloning vector DNA with a restriction enzyme such as EcoRI. The exogenous DNA segment is purified using standard techniques such as one or more of electrophoresis or HPLC (Velander, et al., *Annals. New York Academy Sciences*, 665, 391–403 (1992)). In general, the DNA segment is precipitated and washed thoroughly before being reconstituted in a sterile injection buffer. For example, the genetic material is precipitated with ethanol, washed free of salts with 80% ethanol/water solution, and then reconstituted in a sterile, filtered injection buffer (10 mM Tris-HCL, 1 mM EDTA, pH 8.0) (TE).

The concentration of the exogenous DNA segment in the buffer is determined using methods standard in the art. For example, the concentration of the DNA segment in the buffer solution is determined by measuring the ultra-violet light absorbance at a standard wavelength, e.g., 260 nanometers. The concentration is based upon absorbance values obtained from a control blank (buffer solution) and standard dilution concentrations from a DNA segment of the same size as the DNA segment in the buffer solution. Alternatively, DNA fragment size and concentration are accurately estimated by agarose gel electrophoresis with a 1 kb (kilobase) ladder (Sigma Chemical Co., Cat. # A2929, St. Louis, Mo.) and Hind III digest of lamda DNA standards (Sigma Chemical Co., Cat. # D9780, St. Louis, Mo.), followed by ethidium bromide staining.

Prior to storage or injection, the DNA is diluted to an appropriate concentration. For example, DNA is diluted for storage with TE buffer to a concentration two (2) times the final value to be used for injecting (this translates into about 30 µg/ml for a 6.0 kb DNA segment). This solution concentration of DNA is referred to below as a "2X" DNA solution. DNA solutions are conveniently stored at reduced temperatures until needed for absorption or injection. For example, DNA solutions are stored in the TE buffer at about −20° C.

The polycation for formation of polycation/DNA complexes may comprise any polymeric molecule capable of forming a complex with DNA by electrostatic attraction. This includes both homo- or hetero- polycations with complexing ability. Some monomeric units making up the polycation may be neutral or even have a negative charge. A polycation will typically have a net positive charge at the pH for forming a complex with DNA. Preferred polycations are polymers of amino acids, but polymers of amino acids are not essential since they are merely one example of the class of polycations. A particular polycation may be selected because it has one or more of the following properties: DNA charge neutralization, protection of DNA from endonuclease or DNAse digestion, or an ability to aid in the formation of DNA aggregates. The length of the polycation polymer is not critical. The optimum chain length for a particular polycation and DNA segment is readily determined by routine experimentation.

A preferred polycation for forming a polycation/DNA complex is a polymer composed of a D- or L-amino acids such as polylysine or polyarginine. Preferred amino acid polycations other than polylysine or polyarginine are those having similar charge neutralizing effects upon DNA molecules. Mixed (hetero) amino acid polymers (composed of more than one amino acid type) are also preferred which have a net positive charge at the pH for forming a complex with DNA. The amino acids comprised in a mixed polymer may be neutral, acidic, or basic. Preferred mixed amino acid polymers are those having a high percentage of lysine or arginine subunits. Polycation polymers may comprise either histone polypeptides or hetero-multimers of histone polypeptide subunits, which will electrostatically bind DNA. Other naturally occurring or artificially synthesized polycations of polyamino acids which bind DNA may be utilized.

A 1 mg/ml polylysine stock solution for preparing polycation/DNA complexes may be obtained by mixing a lysine polymer (e.g., polylysine bromide having an average length of 51 lysine bromide residues (Sigma Chemical Co., Cat.# P6516, lot# 128F-5033); or polylysine bromide having an average length of 17 lysine bromide residues (Sigma Chemical Co., Cat.# P-0879, lot# 111H-5520)) and an appropriate injection buffer (such as the TE buffer described above). The 1 mg/ml stock solution is diluted with TE (or other acceptable injection buffer) until a desired polylysine stock reagent is obtained. A preferred polycation reagent is obtained by mixing a polylysine solution and a 2X exogenous DNA segment solution is such proportions that a polycation/DNA complex with a 2:1 molar charge ratio (i.e., a 4X polylysine solution) results.

The concentration of DNA in a 1X DNA segment solution is about 15 µg/ml for a 6.0 kb DNA segment. Thus, a 4X polylysine solution for forming a polycation/DNA complex with a 1X 6.0 kb DNA segment solution corresponds to a polycation reagent solution having a polylysine concentration of about 26.4 µg/ml. Similarly, for a 1X 6.0 kb DNA segment solution, a corresponding 2X polylysine solution would have about 13.2 µ/ml of polylysine and a corresponding 1X polylysine stock solution would have about 6.6 µg/ml of polylysine. Polylysine stock solutions are conveniently stored at about −20° C. until used.

Both DNA and polylysine solutions are handled and stored in sterile containers. For example, sterile microcentrifuge tubes of about 0.5 ml volume (Denville Scientific, Denville, N.J.) are conveniently used for both handling and storage.

Polycation/DNA complexes for cytoplasmic injection or cellular absorption may be prepared as follows.

When equal volumes of polycation solution and DNA solution are mixed, the volume of the mixture is twice that of either starting solution. Thus, the concentration of either polycation or DNA per unit volume in the mixture is one-half of the concentration per unit volume of the corresponding polycation or DNA starting solution. Accordingly, to produce a 1X polycation and DNA mixture, the starting polycation and DNA solutions are each 2X solutions.

A 1X polylysine and DNA mixture with a molar charge ratio of 1:1 is formed by mixing equal volumes from each 2X stock solution (DNA and polycation, each in a buffer) described above. For example, 50 µl of a 2X solution of 6.0 kbp DNA (30 µg/ml) and 50 µl of a 2X polylysine stock solution (13.2 µg/ml) are mixed to form a 100 ml mixture of polylysine and DNA at a 1:1 molar charge ratio.

The 100 µl 1X polylysine and DNA mixture, described above, forms a 100 µl 1X polycation/DNA complex solution when it is allowed to stand for at least about 15 minutes. The result is a 100 µl polylysine/DNA complex solution having 15 µg/ml of 6.0 kbp DNA and 6.6 µg/ml of polylysine present, wherein the polycation/DNA complex has a 1:1 molar charge ratio and essentially no net charge.

As the size of the molecules in the solutions which form the complex will vary, the optimum time for allowing the complex to form from the mixture will also vary. Thus, the time required to allow polycation/DNA complex formation may be varied to obtain optimum results for a particular polycation/DNA complex. The optimum time required will depend upon the length and type of polycation and DNA being complexed.

The extent of complex formation in the polycation and DNA mixture solution is demonstrated by electrophoresis of the solution on an ethidium bromide-stained agarose gel. No band is observed which corresponds to the size of the DNA segment of the mixture, when there is complete formation of a polycation/DNA complex having a 1:1 molar charge ratio. Absence of a band is presumably due to polylysine neutralizing negative charges on DNA. DNA complexed with a poly-cation will not migrate on an agarose gel in an electric field.

The presence of the non-migrating DNA segment in the complex may be verified by amplification of a specific target sequence contained within the DNA segment. Amplification by standard oligonucleotide procedures with PCR primers specific for the DNA target sequence, followed by a hybridization assay with a probe specific for the target sequence allows this determination.

The polycation/DNA complexes may be loaded into microinjection pipettes for injection into a recipient cell. Alternatively, the polycation/DNA complexes are added to a cell culture medium for cellular absorption into a recipient cell.

For cellular absorption, the concentration of a polycation/DNA complex may be varied in a cell culture medium to obtain an optimum yield of transgenic cells. For a particular cell being transformed a 2X–50X concentration (see the above discussion for the meaning of X) of a polycation/DNA complex may be ideal. A 2X–10X concentration is preferred.

Applicants have found that the molar charge ratio of a DNA/polycation complex produces a change in electrochemical properties of the resulting DNA/polycation complex. The substantial neutralization of the negative DNA charge allows the exogenous DNA of the complex to become associated with, and subsequently transported across, the pronuclear or nuclear envelope. The reduction in net negative charge also allows the recipient cell to absorb DNA across a cellular membrane.

Moreover, applicants have found that complex formation with a polycation tends to stabilize DNA against degradation in the recipient cell. The increased stability allows for greater association of exogenous DNA with a cell's endogenous DNA to result in a transgenic organism.

Applicants have determined that some DP-51 polylysine/DNA complexes are too large to be efficiently discharged from microinjection pipettes routinely used for pronuclear microinjection. Therefore, the optimal cytoplasmic injection of such DP-51 polylysine/DNA complexes is achieved with pipettes which are slightly larger. Accordingly, the optimum pipette size for cytoplasmic microinjection of polycation/DNA complexes is readily determined by routine experimentation. For example, the PCR assay described above can be conveniently performed upon single cells immediately after injection to determine if adequate intact DNA (from polycation/DNA complexes) was injected. Based upon results from PCR assays, the microinjection pipette diameter can be varied to provide optimum injection of the polycation/DNA complexes. Alternatively, the size of the polycation, which is part of the polycation/DNA complex, may be varied to allow cytoplasmic microinjection with smaller diameter pipettes. For example, the size and/or deformability of the polylysine/DNA complexes produced by mixing DP-17 polylysine (17 lysine bromide residues) and DNA permits efficient injection of the complex (and thus the DNA) into the cytoplasm via pipettes of the size routinely used in pronuclear microinjection procedures.

DNA from a polycation/DNA complex is inserted into an organism's genetic makeup by injecting the complex or absorbing it into the cytoplasm or perivitelline space of a recipient cell. Preferably, genetic transformation of an organism is obtained by inserting a polycation/DNA complex into the cytoplasm of an embryonic cell via microinjection. A more preferred method is where a polycation/DNA complex is injected directly into the cytoplasm of a zygote or an unfertilized egg.

One-celled zygotes for transformation in accordance with the present invention may be obtained by standard procedures well-known in the art.

To obtain fertilized animal eggs for transformation, females are superovulated by interperitoneal injection of serum gonadotropin (e.g., pregnant mare's serum gonadotropin), followed by injection of chorionic gonadotropin (e.g., human chorionic gonadotropin). See, general procedures of Brinster et al., *Growth, Nutrition and Metabolism of Mammalian Cells in Culture*, Vol. 2, 251–286, New York Academic Press (1972) and Wu, et al., *Methods of Enzymology*, Vol. 101, 411–433, New York Academic Press (1983). The superovulating females are bred to males. Alternatively, unfertilized eggs are isolated and fertilized in vitro by standard in vitro fertilization procedures. Fertilized one-celled embryos are collected by standard methods, such as those described by Brinster, et al., *Cell* 27, 223–231 (1981); Brinster, et al., *Proc. Natl. Acad. Sci. U.S.A.* 82 4438–4442 (1985)); and Wu, et al., *Methods of Enzymology*, Vol. 101, 411–433, New York Academic Press (1983). Standard gamete fusion methods (e.g., polar body-egg fusion, nuclear transfer, or embryo cloning) may also be used to produce an embryo or zygote.

Fertilized embryos or unfertilized eggs that are surrounded by cumulus (granulosa) cells are removed from a female by tearing the ampulla region of a female's oviduct. The cumulus mass is dissolved by washing the embryos or eggs in an appropriate medium contain hyaluronidase. For example, the embryos or eggs are washed in a sterile container having about 0.2 mg/ml hyaluronidase (Sigma Chemical Co., Cat.# H4272 St. Louis, Mo.) per 3 ml of Brinster's Medium (M2) (See, Brinster et al., *Growth, Nutrition and Metabolism of Mammalian Cells in Culture*, Vol 2, 251–286, New York Academic Press (1972)).

The embryos or eggs are then washed in a fresh container of M2 medium. If the harvested eggs are unfertilized, they are then fertilized by standard in vitro fertilization methods, and the resulting embryos again washed in M2 medium. M2 medium may also be obtained from Sigma Chemical Co., Cat. # M5910 (St. Louis, Mo.).

Embryos are maintained in a holding medium while being injected. An example of a holding medium for injection of one-celled embryos is M2 medium that is modified by substitution of 25 mM hepes buffer (pH 7.4) (e.g., Sigma Chemical Co., Cat. # H6147, (St. Louis, Mo.)) for the bicarbonate. For injection one-celled embryos are placed in a sterile container (e.g., on the lid of a sterile 100 mm petri dish) in a 300 µl drop of the above described holding medium. The surface of the medium is covered with an oil such as paraffin oil (e.g., Sigma Chemical Co. Cat. # M8410 (St. Louis, Mo.)) or silicone oil (e.g., Sigma Chemical Co. Cat. # DMPS-5X, (St. Louis, Mo.)) having a viscosity of about 50 centistokes (1 centistoke=$10^{-6}$ m$^2$/sec) to prevent medium evaporation.

For injection, the embryos are held with a heat-polished glass pipette of appropriate diameter and smoothness. For example, holding pipettes having an outside diameter of about 30 µm are made from filamented glass capillaries having an outside diameter of about 1.1 mm (e.g., World Precision Instruments). The size of a holding pipette may be optimally varied to accommodate differences in the size of embryos. Injection pipettes are obtained, for example, by drawing pipettes using a micropipette puller, followed by polishing. Thus, finely drawn, sterile filamented glass capillaries are obtained to use as injection needles. Micropipette pullers and polishers are readily available in the art.

The polycation/DNA complexes as described above are inserted into one-celled embryos as follows.

Microinjection of the embryos is carried out under magnification. The embryos are visualized using appropriate optics, e.g., Hoffman Modulation Contrast Optics at 200× magnification fitted to a Zeiss (Carl Zeiss, Model ICM-35) inverted microscope. Each embryo is, in turn, held within a pipette and visualized. A loaded injection pipette is prepared as described above. For example, solutions of polylysine/DNA complexes (prepared as described above) are back-loaded via pasteur pipettes into a microinjection pipette. The loaded pipette is inserted within the holding pipette and brought into view of the optics. Each embryo is injected by inserting the tip of the injection pipette into the cell and injecting into the cell a desired volume of polylysine/DNA complex solution.

Each one-celled embryo is injected with about 1–30 picoliters, preferably 5–15 picoliters, and most preferably about 10 picoliters, of the polylysine/DNA complex solution. The desired volume is injected into the cytoplasm of each embryo in the microdrop using a volume controlling injector, e.g., an Eppendorf (Model 5242) pneumatically controlled microinjector. Special care should be taken that the injector does not puncture either the nuclear or pronuclear membrane of the one-celled embryo.

Transfer of injected embryos to pseudopregnant females, their incubation, and birth is as follows.

After injection, embryos are washed in fresh media and transferred into the oviduct or uterus of a pseudopregnant female using standard procedures. For example, procedures according to Rafferty, *Methods in Experimental Embryology of the Mouse*, Johns Hopkins, Baltimore (1970) and Brinster et al., *Proc. Natl. Acad. Sci. U.S.A.* 82 4438–4442 (1985) may be used. Procedures of Wu, et al., *Methods of Enzymology*, Vol. 101, 411–433, New York Academic Press (1983) may be followed to assure embryo transfer without competition or confusion with non-injected embryos of pseudopregnant females.

After birth, the resulting animals are allowed to mature and then tested for the transgene as follows.

DNA is isolated from animals by methods previously described (see for example, Brinster, et al., Cell 27, 223–231 (1981); Brinster, et al., Proc. Natl. Acad. Sci. U.S.A. 82 4438–4442 (1985)); and Wu, et al., *Methods of Enzymology*, Vol. 101, 411–433 New York Academic Press (1983). The DNA preparations are analyzed for the presence of the inserted genetic construct by gene amplification (e.g., by PCR) followed by ethidium bromide stained agarose gel electrophoresis to compare the size of the amplified DNA segment with that from a positive control. These procedures are well-known in the art, (see for example, (Sakai, et al., *Science* 230 1350–1354 (1985)). For further verification, DNA from the animal can be digested with a restriction enzyme and fractionated on an ethidium bromide-stained agarose gel. The fractionated DNA thus obtained is blotted onto a nitro-cellulose filter and subjected to hybridization with a cDNA probe, which is specific for a segment of the construct. $^{32}$P-labelled probes may be made by the random primer labelling technique described previously (Velander, et al., *Annals. New York Academy Sciences*, 665, 391–403 (1992)). Presence of a band corresponding to the same fragment size as control lanes containing construct DNA verifies the incorporation of the construct DNA by the transgenic animal.

The transgenic animals according to the present invention can be further tested to verify their germline mosaic status as follows.

As a founder animal, the transgenic positive animal is mated with a native animal of the opposite sex, and the resulting offspring are tested for the transgene as described above for the founder animals. For some of the offspring, the DNA samples isolated test positive for the transgene. This indicates that the founder animal possesses the transgene in its germline.

Addition of exogenous genetic material to the genetic make-up of the organism by cytoplasmic injection of a polycation/DNA complex after the zygote has divided into multiple cells may require addition of the material to each of the cells of the zygote. Incomplete or ineffective addition to each of the multiple cells may result in an organism of a non-native phenotype not having the exogenous material incorporated into its genetic make-up in such a manner that it can pass on the desired trait to its offspring.

Thus, the exogenous genetic material is preferably incorporated into a one-cell stage fertilized zygote or a precursor. Non-limiting examples of precursors are oocyte cells, ovum cells, polar body cells, spermatocyte cells, and sperm cells.

The often dense genetic material of a mature sperm cell may be decondensed according to known methods. See for example Wagner et al., *Archives of Andrology*, 1 31–41 (1978). Preferably, a disulfide reductant is used for decondensation when exogenous genetic material is added to a mature sperm cell. Decondensation enhances incorporation of exogenous genetic material.

The exogenous genetic material can be added to a fertilized or unfertilized ovum or its precursors. Preferably, the exogenous genetic material is added in the form of polycation/DNA complex. Even more preferred is to add the exogenous genetic material to a recently fertilized (or recently activated by parthenogenesis) one-celled zygote stage.

The actual developmental stage of the organism at which the exogenous genetic material is inserted into the genome may be varied from organism to organism as desired.

The non-limiting examples below illustrate the production of transgenic mice by injecting either DNA alone or DNA complexed with a polycation by electrostatic interaction into the cytoplasm of one-cell mouse embryos.

EXAMPLE 1

Production and Testing of Transgenic Mice

A. Obtaining DNA for Insertion Into Embryos

A DNA hybrid construct was prepared consisting of a 1.8 kbp segment of structural DNA encoding human protein C inserted between a 2.6 kbp segment of 5' non-coding DNA and a 1.6 kbp segment of 3' non-coding DNA corresponding to the mouse whey acidic protein gene (Campbell, et al., Nucleic Acids Res., 12, 8685–8697 (1984); Hennighausen, et al., Nucl. Acids Res. 10, 3633–3744 (1982); Dandekap, et al., Proc. Natl. Acad. Sci. U.S.A. 79 3987–3991; Hennighausen, et al., Nucl. Acids Res. 10, 2677–2684 (1982); Andres et al., Proc. Natl. Acad. Sci. U.S.A. 84, 1299–1303 (1987); and Velander, et al., *Annals. New York Academy Sciences*, 665, 391–403 (1992)).

The construct (designated as WAPPC-3) was cloned according to Maniatis, et al., Molecular Cloning: A Laboratory Manual (Cold Spring Harbor Laboratory, Cold Spring Harbor, N.Y.) (1982). The plasmid construct was cloned into a pUC-19 plasmid vector (Stratagene, Inc., La Jolla, Calif.) to yield a pUC-19/WAPPC-3 plasmid vector. JM109 *E. coli* cells (GIBCO BRL., Bethesda, Md.) were transformed with pUC-19/WAPPC-3, which reproduced in the JM109 *E. coli* cells.

The transformed JM109 *E. coli* cells were lysed by alkaline lysis according to the standard lysis procedures of Maniatis, et al., Molecular Cloning: A Laboratory Manual (Cold Spring Harbor Laboratory, Cold Spring Harbor, N.Y.) (1982)). The DNA construct of the plasmid was isolated and purified by methods standard in the art as follows.

The cloning vector was digested away from the DNA construct segment with the EcoRI restriction enzyme to yield a DNA segment. The DNA segment was further purified using high pressure liquid chromatography (HPLC) (Velander, et al., *Annals. New York Academy Sciences*, 665, 391–403 (1992)). The DNA segment was precipitated with ethanol and then washed free of salts with an 80% ethanol/water solution. The DNA segment was recovered and reconstituted in a sterile, filtered injection buffer (10 mM Tris-HCL, 1 mM EDTA, pH 8.0) (TE).

The concentration of the DNA segment in the buffer solution was determined by measuring the ultraviolet light absorbance at a wavelength of 260 nanometers. The concentration was based on absorbance values obtained from a control blank (buffer solution) and standard dilution concentrations from a DNA segment of the same size as the DNA segment in the buffer solution.

Alternatively, the concentration is determined by ethidium bromide stained agarose gel electrophoresis having a 1 kb ladder resolution (Sigma Chemical Co. Cat.# A2929, St. Louis Mo.) and Hind III digest of lamda DNA standards (Sigma Chemical Co. Cat.# D9780, St. Louis, Mo.). The width and brightness of bands on the ethidium bromide stained agarose gel correspond to concentrations of DNA in the buffer solution.

After determining the concentration of the DNA segment in the TE buffer solution. The DNA segment solution was then diluted by TE buffer to a concentration two (2) times the final value to be used (30 µg/ml) in DNA injection. The DNA solutions were stored in TE buffer at −20° C. until used.

B. Preparing a Polycation Solution for Use in Preparing Polycation/DNA Complexes A 1 mg/ml polylysine stock solution was made by mixing a lysine polymer (i.e., a poly-1-lysine having an average length of 51 lysine bromide salt residues (Sigma Chemical Co., Cat.# P6516, lot# 128F-5033) and TE injection buffer as described in part A, above. The 1 mg/ml stock solution was diluted with TE injection buffer until a 4X concentration was obtained (a poly-L-lysine concentration of 26.4 µg/ml). Similarly, a 2X polylysine stock solution having 13.2 µg/ml of poly-L-lysine was obtained by diluting 4X stock solution with TE buffer to one-half concentration. The polylysine stock solutions were conveniently stored at −20° C.

C. Preparing a Polycation/DNA Complex Solution From Polycation and Insertion DNA Solutions Polylysine/DNA complexes were formed by mixing equal volumes of each 2X stock solution (from parts A and B, above) and letting the combined solutions stand at least 15 minutes for the complex to form. Formation of complexes was demonstrated by agarose gel electrophoresis of the solutions followed by ethidium bromide staining. Absence of a band corresponding to the size of the DNA construct is due to the polylysine neutralizing the negative charge on the DNA. The neutralized DNA of the polycation/DNA complex did not migrate in an electric field. The presence of DNA (in the complexes of the solution which did not migrate in an electric field) was further checked by successful PCR amplification of a specific target sequence contained within the WAPPC-3 construct.

In this 1X polylysine/DNA complex solution, the concentrations of polylysine and DNA were 6.6 µg/ml and 15 µg/ml, respectively. The polylysine/DNA complex solutions were handled and stored in sterile 0.5 ml microcentrifuge tubes (Denville Scientific, Denville, N.J.).

D. Obtaining Fertilized Mouse Embryos

Immature female mice (CD-1 white Swiss mice; Charles River Laboratories, Wilmington, Mass.) 24 to 30 days of age were superovulated by interperitoneal injection of 10 I.U. pregnant mare's serum gonadotropin (PMSG), followed by 5 I.U. of human chorionic gonadotropin (HCG) 46 to 48 hours later (as described in Brinster et al., *Growth, Nutrition and Metabolism of Mammalian Cells in Culture*, Vol 2, 251–286, New York Academic Press (1972), and Wu, et al., *Methods of Enzymology*, 101, 411–433, New York Academic Press (1983)). The females were bred to CD-1 males between 3 and 6 months of age. One cell embryos were collected 21–24 hours after HCG injection by the methods described by Brinster, et al., *Cell* 27, 223–231 (1981); Brinster, et al., *Proc. Natl. Acad. Sci. U.S.A.* 82 4438–4442 (1985)); and Wu, et al., *Methods of Enzymology,* 101, 411–433, New York Academic Press (1983).

E. Preparation Of Mouse Embryos for Injection

The embryos from part D, above, that were surrounded by cumulus (granulosa) cells were removed from a female mouse by tearing the ampulla region of the mouse's oviduct. The cumulus mass was dissolved by washing the embryos in a sterile 35 mm petri dish containing 0.2 mg/ml hyaluronidase (Sigma Chemical Co., Cat.# H4272, St. Louis, Mo.) in 3 ml of Brinster's Medium (M2) (See, Brinster et al., *Growth, Nutrition and Metabolism of Mammalian Cells in Culture*, Vol 2, 251–286 New York Academic Press (1972)). The embryos were then washed in a fresh dish of M2 and placed into a 300 µl drop of new medium (M2 medium modified by substituting 25 mM hepes buffer (pH7.4) (Sigma Chemical Co. Cat.# H6147) for bicarbonate) on the lid of a sterile 100 mm petri dish and covered with paraffin oil (Sigma Chemical Co. Cat.# M8410; viscosity about 50 centistokes; 1 centistoke=$10^{-6}$ $m^2$/sec) to prevent medium evaporation.

F. Microinjecting Mouse Embryos with Exogenous DNA

Finely drawn, sterile microinjection pipettes were obtained by drawing filamented glass capillaries, with a Kopf micropipette puller (Model 720) and polishing via a Narashige microforge (Type BK85). The 1X solution of polylysine/DNA complexes of part C, above, was backloaded into these finely drawn capillary pipettes to provide loaded microinjection pipettes.

The embryos obtained in part E, above, were held within a heat-polished glass pipette made from filamented glass capillaries (World Precision Instruments) having an outside diameter of about 30 µm. The held embryos were visualized for microinjection under a Hoffman Modulation Contrast Optics at 200× magnification fitted to a Zeiss (Carl Zeiss, Model ICM-35) inverted microscope. In turn, each embryo was held within a holding pipette and each embryo was injected by inserting the tip of an injection pipette (a finely drawn filamented glass capillary) into the embryo.

About 10 picoliters of solution was injected into the cytoplasm of each embryo in the microdrop using an Eppendorf (Model 5242) pneumatically controlled microinjector. Special care was taken that the injection did not puncture male or female pronuclear membranes of any one-celled mouse embryo. The 1X polylysine/DNA solution was injected into seventy-one mouse embryos, with fifty mouse embryos surviving the injection procedure.

G. Transfer of Injected Embryos to Pseudopregnant Female Mice, In Vivo Incubation, and Birth The DNA injected embryos of part F, above, were washed in fresh M2 medium and transferred into the left oviduct of two pseudopregnant female mice using the procedures of Rafferty, *Methods in Experimental Embryology of the Mouse*, Johns Hopkins, Baltimore (1970) and Brinster et al., *Proc. Natl. Acad, Sci. U.S.A.* 82 4438–4442 (1985)). The general techniques of Wu, et al., *Methods of Enzymology*, 101, 411–433 New York Academic Press (1983) were followed to assure injected embryo transfer without competition with non-injected embryos of the pseudo-pregnant mice. Twenty days after the embryos were transferred, each of the two surrogate mother females gave birth to thirteen pups. After birth the pups were allowed to mature for twenty-one days and were then weaned and separated from the surrogate mothers. Thus, a total of twenty-six pups were provided for DNA testing from the original surviving fifty embryos that were injected with the polylysine/DNA complex and transferred to surrogate mothers.

H. Testing Pups for Transgenic DNA

To test for the transgene, after weaning DNA was isolated from the pups of part G, above, by methods previously described (Velander, et al., *Annals. New York Academy Sciences*, 665, 391–403 (1992)). The DNA preparations were analyzed for the presence of the WAPPC-3 construct by a PCR technique described previously in Velander, et al., *Proc. Natl. Acad. Sci. USA* 89, 12003–12007 (1992). One of the twenty-six mice born from the two litters tested positive for the transgene. For further verification, ten μg of DNA from this mouse was then digested with the restriction enzyme EcoRI and fractionated on an ethidium bromide-stained agarose gel. The fractionated DNA was blotted onto a nitrocellulose filter and subjected to hybridization with a human Protein C $^{32}$P-cDNA probe labeled according to the random primer labelling technique of Velander, et al., *Proc. Natl. Acad. Sci. USA*. 89 12003–12007 (1992). The presence of a band corresponding to construct DNA indicated incorporation of a construct into the mouse genome.

I. Founder Transgenic Mouse Verification by F1 Progeny

The transgenic mouse of Example 8 was tested to verify its germline mosaic status as follows.

The transgenic positive mouse of part H, above, was mated with a native control male, and the resulting offspring pups were weaned at twenty-one days of age. DNA samples isolated from tissue biopsies from these offspring were analyzed for the WAPPC-3 transgene using the same PCR procedures as in part H, above. One of the pups from this litter tested positive for the transgene, thus indicating that the founder female of part H was a capable of passing the transgene to her offspring. Since less than 50% of her offspring tested positive for the transgene, she was a germline mosaic.

EXAMPLE 2

The procedure of Examples 1, parts A–H, was repeated, resulting in two additional transgenic animals containing the WAPPC-3 transgene.

EXAMPLE 3

The procedure of Example 1, parts A–H, was repeated, resulting in three additional transgenic animals containing the WAPPC-3 transgene.

EXAMPLE 4

The procedure of Example 1, parts A–H, was repeated, but the polylysine/DNA complex was injected at a DNA concentration of 50 μg/ml and a molar charge ratio of 1:1. Of the 9 pups born, 8 pups tested positive for the WAPPC-3 transgene by PCR assay. Six pups were confirmed positive for the WAPPC-3 transgene by southern hybridization. See FIG. 6 for positive southern hybridization.

EXAMPLE 5

The procedure of Example 1, parts A–H, was repeated, but the polylysine/DNA complex was injected at a DNA concentration of 50 μg/ml and a molar charge ratio of 2:1. Of the 11 pups born, 2 pups tested positive for the WAPPC-3 transgene by PCR assay. Both of these pups were confirmed positive for the WAPPC-3 transgene by southern hybridization. See FIG. 6 for positive southern hybridization.

COMPARATIVE EXAMPLE 1

As a control, the procedure of Examples 1 was followed repeatedly except that naked DNA rather than polycation/DNA complex was microinjected into cytoplasm of the mouse embryos. Of the thirty-nine control pups born, none contained the transgene, as determined by PCR procedures described above in Example 1.

COMPARATIVE EXAMPLE 2

To compare the efficiency of producing transgenic mice by the cytoplasmic injection polylysine/DNA versus pronuclear injection of DNA, the procedures of Examples 1 were followed except that pronuclear injection procedures using DNA alone (at the same concentration injected in Examples 1) was used rather than the cytoplasmic injection of polycation/DNA complexes. Of the twenty-three pups born from pronuclear injection procedures, five contained the transgene, as analyzed by the PCR procedures described in Example 1.

SUMMARY OF RESULTS AND COMPARISONS OF THE EXAMPLES

The results for: (1) cytoplasmic injection of polylysine/DNA complexes; (2) cytoplasmic injection of just DNA; and (3) pronuclear injection of just DNA are summarized as follows, and tabulated in Table 1.

Cytoplasm (Polylysine/DNA) Injection: Example 1 and Comparative Examples 1–2 a total of 492 embryos were injected;

a total of 303 embryos survived and were transferred to surrogate mothers;

62 percent of the embryos injected survived injection a total of 91 pups were born;

30 percent of the embryos transferred resulted in live-birth pups 16 of the 91 pups born were transgenic 18 percent of the pups born were transgenic 6.3 percent of the transferred embryos were transgenic Cytoplasm (DNA Only) Injection: Comparative Example 1 a total of 253 embryos were injected;

a total of 147 embryos survived and were transferred to surrogate mothers;

58 percent of the embryos injected survived injection a total of 39 pups were born;

27 percent of the embryos transferred resulted in live-birth pups 0 of the 39 pups born were transgenic 0 percent of the pups born were transgenic 0 percent of the transferred embryos were transgenic Pronuclear (DNA) Injection: Comparative Example 2 a total of 262 embryos were injected;

a total of 143 embryos survived and were transferred to surrogate mothers;

55 percent of the embryos injected survived injection a total of 23 pups were born;

16 percent of the embryos transferred resulted in live-birth pups 5 of the 23 pups born were transgenic 22 percent of the pups born were transgenic 3.5 percent of the transferred embryos were transgenic

TABLE 1

| Parameter | Injection Site | | |
|---|---|---|---|
| | Pronuclear (DNA only) | Cytoplasm (polylysine/DNA) | Cytoplasm (DNA only) |
| Embryos Injected | 262 | 492 | 253 |
| Embryos Transferred | 143 | 303 | 147 |
| Percent Embryos Surviving | 55 | 62 | 58 |
| Pups Born | 23 | 91 | 39 |
| Number Born Transgenic | 5 | 16 | 0 |
| Percent Born Transgenic | 22 | 18 | 0 |
| Percent Embryos Transgenic | 3.5 | 6.3 | 0 |

EXAMPLE 6

Cytoplasmic and Pronuclear Microinjection Effects on In Vitro Embryonic Viability The effects of cytoplasmic and pronuclear micro-injection on in vitro viability of injected mouse embryos were studied as follows.

Embryos were provided and injected with DNA according to cytoplasmic and pronuclear microinjection techniques described in Example 1, and Comparative Example 2, as follows: (i) cytoplasmic injection of polylysine/DNA complexes with 1.5, 15, and 50 µg/ml of DNA, respectively; (ii) pronuclear microinjection with 15 µg/ml of DNA; and (iii) cytoplasmic injection with 15 µg/ml of uncomplexed DNA. Between 15 and 25 embryos were placed in a 10 µl microdrop of CBZ culture medium in each treatment and maintained under culture condition. The embryos were periodically observed with a stereo-microscope for up to 96 hours for blastocoel development. Embryos were judged as having developed to the blastocyst stage when a fully formed blastocoel cavity was detected.

The results are set forth in Table 2, below.

TABLE 2

| Injection Site | Ratio of Surviving Embryos to Total Embryos Injected | | |
|---|---|---|---|
| | 1.5 µg/ml DNA | 15 µg/ml DNA | 50 µg/ml DNA |
| Cytoplasm | 27/42 (64.3%) | 16/24 (66.7%) | 7/20 (35.0%) |
| Pronucleus | 27/100 (27.0%) | 7/40 (17.5%) | — |
| Control | — | 51/74 (68.9%) | — |

"—" means data in that position not obtained

EXAMPLE 7

Cytoplasmic Injection With Polycation/DNA Complexes and Naked DNA: Effects on In Vitro Transgene Detection The effects of cytoplasmic injection with polycation/DNA complexes and naked DNA on in vitro embryonic detection of a transgene were determined from mouse blastocysts cultured from a one-cell stage. Presence or absence of the construct DNA was determined from blastocysts cultured after cytoplasmic injection with polycation/DNA complexes or naked DNA.

Embryos were provided and injected by the cytoplasmic microinjection technique of Example 1. Injected was DNA at concentrations of 1.5, 15, and 50 µg/ml of DNA, wherein each of the polylysine/DNA complexes had a molar charge ratio of 0:1 (uncomplexed or naked DNA), 0.5:1, 1:1, and 2:1, respectively. For comparison, a control set of uninjected embryos was exposed to the same culture condition as the injected embryos, but control embryos were not injected with any DNA. Between 15 and 25 embryos were placed in a 10 µl microdrop of CBZ culture medium in each treatment. After injection the embryos were maintained under culture conditions for 96 hours.

After 96 hours, detection of the transgene in the embryos by PCR was as follows. Embryos were removed from an incubator after 5 days of in vitro culture and rinsed with 3 ml of M2 holding medium in three (3) successive 35 mm petri dishes. They were then moved with a sterile borosilicate glass pasteur pipette into sterile 0.5 ml microcentrifuge tubes containing 5.0 µl of embryo lysing buffer (ELB: 20 mM tris-HCL, pH 8.3; 0.9% Triton x-100; 0.9% nonidet P40; 400 µg/ml Proteinase K). The embryos were transferred with less than µl of medium since the surface tension of the ELB was allowed to pull the embryo out of the pipette tip. The ELB containing the embryo was then overlayed with 25 µl of paraffin oil to prevent evaporation during the thermocycling PCR reaction. The microcentrifuge tubes containing the embryos were stored at −85° C. until PCR analysis. Reactions were carried out in 25 µl volumes (10 mM Tris-HCL pH 8.3; 50 mM KCL; 0.1% Triton X-100; 0.2 mM each of dGTP, dATP, dCTP, dTTP; 1.5 mM $MgCl_2$; 0.5 µM each of oligonucleotide primer; and 0.625 units of Taq Polymerase). The tube contents were thawed and soaked for 30 minutes at 55° C. for maximum Proteinase K activity to digest cellular and nuclear protein and therefore release the embryonic DNA into solution. The proteinase K was then heat inactivated by as soaking step at 98° C. for 10 minutes. The temperature was lowered to 85° C. for the addition of 20 µl of reaction mixture. The tubes were subjected to 50 cycles of denaturation at 96° C. for 15 seconds, annealing at 55° C. for 2 minutes, and elongation at 75° C. for 30 seconds.

The DNA amplification products from the above procedures were visualized with ethidium bromide stained agarose gel electrophoresis. The 70 ml gels consisted of 1% agarose (type LE, FMC), and 0.5 µg/ml ethidium bromide in TAE buffer (40 mM Tris-Acetate, 1 mM EDTA, pH 8.1). Electrophoresis was conducted with a 11 cm×14 cm electrophoresis unit (Gibco-BRL, Model Horizon 11–14) at 50 volts for 30 minutes. Gels were photographed with a 4" by 5" polaroid camera under ultraviolet illumination.

The results are set forth in Table 3, below.

TABLE 3

| | Ratio of Transgenic Embryos to Total Embryos Analyzed | | |
|---|---|---|---|
| Charge ratio | 1.5 µg/ml DNA | 15 µg/ml DNA | 50 µg/ml DNA |
| 2:1 | 1/55 (2.0%) | 17/84 (20.0%) | — |
| 1:1 | 6/100 (6.0%) | 1/90 (1.0%) | — |
| 0.5:1 | 0/12 (0%) | 2/40 (5.0%) | 13/17 (76.0%) |
| 0:1 | 0/12 (0%) | 0/12 (0%) | 0/6 (0%) |
| Uninjected Control | — | 76/78 (97.0%)** | — |

*The polycation for the 0.5:1 molar charge ratio complexes had 17 lysine bromide residues per chain, and the polycation for the 2:1 and 1:1 molar charge ratio complexes had 51 lysine bromide residues per chain.
**None of the control embryos are transgenic; this is the ratio of uninjected control embryos in which the endogenous single copy WAP gene was detected by PCR using oligonucleotide primers specific for the endogenous mouse WAP sequences. These were used as a control for the PCR technique to assay for DNA sequences in embryos reaching blastocyst stage to starting total.
"—" means data in that position not obtained

EXAMPLE 8

Concentration Effects: Exogenous DNA Integration Rates for Mice Born From Injected Embryos This example compares effects due to exogenous DNA concentration on DNA genomic integration (or lack of integration) for each of (i) cytoplasmic injection of polycation/DNA complexes, (ii) cytoplasmic injection of naked DNA, and (iii) pronuclear microinjection of naked DNA.

Embryos were obtained and injected with DNA according to cytoplasmic and pronuclear microinjection techniques described in Example 1, and Comparative Example 2, as follows: (i) cytoplasmic injection of poly-lysine/DNA complexes with 1.5, 15, and 50 µg/ml of DNA, wherein each concentration of DNA was injected at a molar charge ratio of 1:1 and 2:1; (ii) pronuclear microinjection with 1.5 µg/ml of naked DNA; and (iii) cytoplasmic injection with 1.5, 15, and 50 µg/ml of un complexed DNA (molar charge ratio 0:1). Since it was well-known in the art that no mice are born after pronuclear injection of DNA at concentrations above about 5 µg/ml, no embryos were pronuclear injected at concentrations of 15 µg/ml and 50 µg/ml. (See, Brinster, et al., *Proc. Natl. Acad. Sci. U.S.A.* 82 4438–4442 (1985)).

The embryos were processed and transferred to the oviducts of pseudopregnant females as set forth in Example 1, parts A–H. The pups were weaned at 21 days of age and DNA was isolated as described in Example 1. The DNA samples were assayed for the presence of the WAPPC-3 construct by PCR as described in Example 1.

The results are set forth in Table 4, below.

TABLE 4

| | Ratio of Transgenic Pups to Total Pups Born | | |
|---|---|---|---|
| Charge ratio | 1.5 µg/ml DNA | 15 µg/ml DNA | 50 µg/ml DNA |
| 2:1 | 0/25 (0*) | 1/26 (4%) | 2/11 (18%) |
| 1:1 | — | 2/22 (9%) | 8/9 (89%) |
| 0:1 | 0/8 (0%) | 0/15 (0%) | 0/16 (0%) |
| Pronuclear | 5/23 (22%) | — | — |

"—" means data in that position not obtained

EXAMPLE 9

Pig Embryo Data

This example demonstrates the effects of cytoplasmic microinjection on in vitro embryonic development of pig embryos to the blastocyst stage after 7 days of culture in NCSU-23 medium. The composition of NCSU-23 medium is set forth in Table 5, below (Courtesy of Robert Petters, Ph.D., North Carolina State University, Raleigh, N.C.)

TABLE 5

| NCSU-23 MEDIA COMPOSITION | | | | | |
|---|---|---|---|---|---|
| Composition | Formula Weight | Grams Per Liter | mM | mOsm | g/100 ml |
| NaCl | 58.44 | 6.35 | 108.73 | 217.46 | 0.0356 |
| KCl | 74.55 | 0.356 | 4.78 | 9.56 | 0.0356 |
| CaCl$_2$ | 110.99 | 0.189 | 1.70 | 5.10 | 0.0189 |
| KH$_2$PO$_4$ | 136.09 | 0.162 | 1.19 | 2.38 | 0.0162 |
| MgSO$_4$.7H$_2$O | 246.47 | 0.294 | 1.19 | 2.38 | 0.0294 |
| NaHCO$_3$ | 84.01 | 2.106 | 25.07 | 50.14 | 0.2106 |
| Glutamine | 146.00 | 0.146 | 1.00 | 1.00 | 0.0146 |
| Glucose | 180.16 | 1.000 | 5.55 | 5.55 | 0.1000 |
| Taurine | 125.10 | 0.876 | 7.00 | 7.00 | 0.0876 |
| Hypotaurine | 109.10 | 0.545 | 5.00 | 5.00 | 0.0545 |
| BSA* | | 4.000 | | | 0.4000 |
| Penicillin | | .060 | | | 0.0060 |
| Streptomycin | | .050 | | | 0.0050 |
| Phenol Red | | .010 | | | 0.0010 |
| Total Osmolarity 305.57 | | | | | |

*BSA = N,O-Bis(trimethylsilyl)acetamide

Pig embryos were obtained by essentially the same procedures set forth in Example 1 except pigs were used instead of mice. The injected and control eggs were cultured in vitro for seven days in NCSU-23 medium instead of being transferred to synchronized females.

The pig embryos were injected by cytoplasmic microinjection techniques as set forth in Example 1 or cultured as uninjected control embryos. Embryos were cytoplasmically injected with polylysine/DNA complexes of WAPPC-3 at 15 µg/ml of DNA, wherein the polylysine/DNA complex was at a molar charge ratio of 2:1. Pronuclear injection was at a DNA concentration of 15 µg/ml at the one-cell stage. Between 10 and 20 embryos were placed in a 10 µl microdrop of NCSU-23 culture medium in each treatment and maintained under culture condition. The embryos were periodically observed with a stereomicroscope for up to 7 days for blastocoel development. Embryos were judged as having developed to the blastocyst stage when a blastocoel cavity was observed. The embryos that developed to the blastocyst stage were tested for the transgene according to PCR techniques set forth above in Example 5. The control embryos that were injected were cultured under the same conditions but were not injected and therefore not subjected to PCR or analyzed for the WAPPC-3 transgene.

The blastocysts to embryo viability ratio results are set forth in Table 6 below.

TABLE 6

| Injection site | Ratio of Surviving Embryos to Total Embryos Injected | | |
|---|---|---|---|
| | 1.5 µg/ml DNA | 15 µg/ml DNA | 50 µg/ml DNA |
| Pronucleus | 9/22 (41%) | — | — |
| Cytoplasm | — | 15/44 (34%) | — |
| Control (Not Injected) | 8/14 (57%) | | |

The results showing the ratio of the number of blastocysts testing positive for the transgene to total blastocysts are set forth in Table 7 below.

TABLE 7

| Injection site | Ratio of Transgene Embryos to Total Blastocysts | | |
|---|---|---|---|
| | 1.5 µg/ml DNA | 15 µg/ml DNA | 50 µg/ml DNA |
| Pronucleus | 2/9 (22%) | — | — |
| Cytoplasm | — | 2/15 (13%) | — |

The above table shows that transgenic embryos are obtained with pig embryos which are cytoplasmic injected with polycation/DNA complexes. Accordingly, the techniques and concepts of the present invention are readily applicable and adaptable to embryos other than those exemplified.

EXAMPLE 10

To further validate the technique for producing transgenic animals using cytoplasmic microinjection of a polycation/DNA complex, the founder animals produced according to Examples 1–3 were mated to control mice. The first six founder animals were mated to control mice using standard cross-breeding techniques. DNA samples were isolated from the progeny by tissue biopsy and assayed for the WAPPC-3 gene as in Examples 1 (e.g., by PCR).

The F1 generation transgenic frequency data is presented in Table 8, below.

TABLE 8

| Founder Mouse | Pups Assayed | Pups Transgenic | Percent Transgenic |
|---|---|---|---|
| 7 | 14 | 1 | 7 |
| 34 | 10 | 6 | 60 |
| 46 | 11 | 11 | 100 |
| 104 | 15 | 0 | 0 |
| 117 | 14 | 0 | 0 |
| 118 | 15 | 0 | 0 |

Three of the six founder mice transmitted the transgene to at least one of their offspring. This indicates that those animals are true germline transgenic animals.

Founder mouse 46 gave an unusual pattern of transgene distribution to his offspring in that each of the progeny was positive for the transgene when assayed by PCR. Of the eleven pups born four appeared to have a distinctly lower copy number than the other seven, which all had a distinctly higher copy number. The relative copy numbers were estimated by the band intensity from PCR amplification products viewed by ethidium bromide-stained agarose electrophoresis. This pattern of transgene segregation among the offspring was probably due to 2 different transgene arrays (or clusters) of different copy numbers being present on two different chromosomes. Therefore, the different arrays were segregated during meiosis.

EXAMPLE 11

F1 Transgenic Mouse Gene Expression Data of Female Mice Produced by Cytoplasmic Polycation/DNA Complex Injection Techniques To further validate the technique for producing transgenic animals using cytoplasmic microinjection of a polycation/DNA complex, four of the F1 transgenic female mice (see Table 8) were mated and their milk assayed for recombinant human protein C expression. The human protein C expression levels in the females' milk were about 30–40 µg/ml.

COMPARATIVE EXAMPLE 3

Gene Expression Data of Female Mice Produced by Pronuclear Injection Techniques

By way of gene expression comparison transgenic mice made with pronuclear injection as set forth in examples 1–13, were provided. Transgenic female founder mice (see Table 8) were mated and their milk assayed for recombinant human protein C expression. The human protein C expression levels in the transgenic founder females' milk were about 30–40 µg/ml.

Accordingly, assessment of the results obtained for Example 11 and comparative Example 3 shows consistent gene expression results for transgenic mice produced by either the pronuclear microinjection techniques or by the cytoplasmic polycation/DNA complex microinjection techniques according to the present invention.

FIGS. 1–6 and the above examples clearly show that transgenic mice capable of passing the transgene to their offspring have arisen from cytoplasmic injection of polycation/DNA complexes.

Moreover, the mechanical procedure of cytoplasmic microinjection offers several advantages over conventional pronuclear microinjection. First, development in vitro of one-cell embryos to the blastocyst stage which have had the DNA/polycation complex injected into their cytoplasm is not different from control one-cell embryos that are not microinjected at all. Second, the polycation/DNA complex has an advantage due to the polycation altering the net charge of genetic material. The charge alteration causes hydrophobic core elements to drive the resulting complex towards association with membrane components within the cell. Moreover, perhaps because of electric charge neutralization, larger amounts of DNA can be injected without significantly affecting the embryo viability.

More pups were born from cytoplasmically injected polycation/DNA complex embryos per embryos transferred as compared to pronuclear injected DNA embryos. This is of particular importance in producing transgenic animals where only a small number of embryos are available and/or gestation periods are long.

Another advantage for cytoplasmic injection as compared to pronuclear injection is that cytoplasmic injection of polycation/DNA complexes does not require the pronuclei to be visualized. This is of particular importance in producing transgenic animals from embryos in which the pronuclei are difficult to see without centrifugation (e.g., pigs and cows). Further, transgenic animals can be produced by cytoplasmic injection polycation/DNA complexes when the pronuclei are difficult to see and the embryos cannot be centrifuged (e.g., goats and sheep). Also, a particular advantage can be recognized in producing transgenic animals from species wherein there is no discernable pronucleus (e.g., fish) or an extremely short pronuclear phase (e.g., chickens).

Moreover, cytoplasmic injection of polycation/DNA complexes is faster and easier than pronuclear microinjection.

The DNA injected is of high enough concentration in the polycation/DNA complex to permit aggregation into either pronuclear or nuclear membrane structures. Aggregates of polycation are stabilized. Thus, insertion of the DNA into the organism's genome takes place before the DNA is degraded or sequestered by the intracellular machinery.

All references cited with respect to synthetic, preparative and analytical procedures represent the state of the art and to the extent necessary are incorporated herein by reference.

The present invention may be embodied in other specific forms without departing from the spirit or essential attributes thereof and, accordingly, reference should be made to the appended claims rather than to the examples in the foregoing specification, as indicating the scope of the invention. It is reasonably expected that an ordinary practitioner in this technical area, upon considering the present description and claims, can provide other equivalent forms of the present invention without departing from the spirit or essential attributes thereof. Accordingly, such variations and permutations are intended to be encompassed within the scope and claims of the present invention.

We claim:

1. A method for inserting a DNA segment into the genome of a recipient animal selected from the group consisting of mammals and birds, comprising:

forming an electrostatic complex of a polycation and a DNA segment, wherein the polycation is present in the complex in an amount effective to neutralize the negative electric charges of the DNA segment to a degree sufficient to allow insertion of the DNA segment into a chromosome of the recipient animal, injecting the polycation/DNA complex in vitro into the cytoplasm of an animal cell selected from the group consisting of an unfertilized ovum and a one-celled embryo, and testing the resulting animal to verify the insertion of the DNA segment into its genome.

2. A method according to claim 1, wherein the animal a mammal.

3. A method according to claim 2, wherein the animal is selected from the group consisting of mice, pigs and cattle.

4. A method according to claim 1, wherein said cell is an unfertilized ovum.

5. A method according to claim 1, wherein said cell is a one-cell embryo.

6. A method according to claim 1, wherein the inserted polycation/DNA complex has a polycation/DNA molar charge ratio of from about 5:1 to about 0.25:1.

7. A method according to claim 6, wherein the molar charge ratio of the polycation/DNA complex is from about 2:1 to about 1:1.

8. A method according to claim 7, wherein the polycation is polylysine and the molar charge ratio of the complex is about 1:1.

9. A method according to claim 1, wherein the electrostatic complex consists essentially of polycation and DNA.

10. A method according to claim 1, wherein said animal is a bird.

11. A method according to claim 10, wherein said bird is a chicken.

12. A method according to claim 3, wherein said animal is a pig.

13. A method according to claim 2, wherein said animal is bovine.

14. A method according to claim 3, wherein said animal is a mouse.

* * * * *